United States Patent [19]

Cowsar

[11] Patent Number: 5,609,859

[45] Date of Patent: Mar. 11, 1997

[54] HAIR RELAXER COMPOSITIONS AND METHODS FOR PREPARING SAME

[75] Inventor: Donald R. Cowsar, Savannah, Ga.

[73] Assignee: Carson Products Company, Savannah, Ga.

[21] Appl. No.: 373,940

[22] Filed: Jan. 13, 1995

[51] Int. Cl.$^6$ .............................. A61K 7/00; A61K 7/06
[52] U.S. Cl. .................. 424/70.4; 424/70.2; 132/204
[58] Field of Search .................. 424/70.4, 70.2; 132/204

[56] References Cited

U.S. PATENT DOCUMENTS

| | | | |
|---|---|---|---|
| 3,864,476 | 2/1975 | Altieri | 424/71 |
| 4,324,263 | 4/1982 | de la Guardia | 132/7 |
| 4,992,267 | 2/1991 | DenBeste | 424/70.4 |
| 5,171,565 | 12/1992 | Akhtar | 424/704 |
| 5,441,729 | 8/1995 | Salce | 424/70.2 |

*Primary Examiner*—Sallie M. Gardner
*Attorney, Agent, or Firm*—Nikaido Marmelstein, Murray & Oram LLP

[57] ABSTRACT

Methods for preparing hair relaxer compositions which comprise a lithium salt and an alkaline earth hydroxide, wherein the lithium salt is in molar excess to the alkaline earth hydroxide. Compositions, kits containing the compositions, and methods for using the compositions are also disclosed.

9 Claims, No Drawings

HAIR RELAXER COMPOSITIONS AND METHODS FOR PREPARING SAME

BACKGROUND OF THE INVENTION

1. Field of the Invention

The invention involves the art of straightening of kinky hair by a lithium relaxer which is made by a novel process.

2. Description of Related Art

Hair relaxer (straightener) compositions presently known to the art are highly alkaline, oil-in-water emulsions which derive their chemical reactivity from either (1) alkali metal hydroxides, (2) quaternary ammonium hydroxides, or (3) guanidinium hydroxide dissolved or suspended in the water phase of these hair-treatment formulations such that the pH values of these emulsions are in the range of from 12 to 14. Among those skilled in the art, it is widely and generally accepted that it is the hydroxide ion, which is the alkaline chemical species common to all three of the above classes, that is the essential active ingredient in these "strong-base" relaxers. In fact, it has be firmly proven that, when inside the cortex of the hair, hydroxide ions readily abstract acidic alpha protons from the cysteine moieties of hair keratin leading to reversible beta elimination of alkyl disulfide (opening of crosslinks) with the concomitant formation of dehydroalanine. It is as these crosslinks continuously open and reform that kinky hair, under mechanical stress, is relaxed to a permanently straight configuration.

Although it is the hydroxide anion which is responsible for initiating the chemical reactions within the hair shaft which lead to straightening, it is the cation with which the hydroxide is associated that has distinguished among the various relaxer types. Prior to 1979, only those one-component ("no-mix") hair relaxer compositions deriving from either sodium or potassium hydroxides were known. In 1979, Carson Products Company (U.S. Pat. No. 4,304,244) introduced the mix type "no-lye" relaxers containing guanidinium hydroxide. Because guanidinium hydroxide is not stable for long periods in aqueous solutions, it must be prepared fresh just before using. Guanidinium hydroxide is generally prepared by mixing an inorganic alkaline earth hydroxide with an aqueous solution of a salt of the strong organic base guanidine, where the anion of this salt is capable of being precipitated by the cation of the alkaline earth hydroxide. In commercially available products of this type, the guanidinium hydroxide is generally prepared using calcium hydroxide and guanidine carbonate.

There are presently two principal defects in all of the prior art hair relaxers. These are as follows: (1) because of their high alkalinity, all can potentially cause scalp irritation and/or injury during the relaxing treatment; and (2) because all are strong-base relaxers capable of dissolving hair keratin, all can overprocess the hair causing irreversible damage to the fibrous keratin structure leading to hair breakage. It has been a continuing goal of researchers in this industry to correct these serious defects.

The scalp irritation potential of chemical relaxers has been reduced somewhat through the formulation of better and better cosmetic emulsions containing high levels of skin-protecting oils such as petrolatum and mineral oil. And, most importantly, it was discovered that relaxers deriving from guanidinium hydroxide are inherently less irritating to the skin and scalp than those deriving from the alkali metal hydroxides. Significantly reducing the irritation potential of hair relaxers, however, remains a major technical challenge to relaxer formulators.

The problem of overprocessing is manifest in the strong-base chemistry of these formulations. With strong bases which are capable of totally dissolving hair, the only control a formulator has in designing safer relaxers is to adjust the concentration of the active ingredient to an optimally effective level. Then, it is up to the user to carefully time the treatment and stop the process when the hair is straight and before it is damaged. Salon professionals learn these skills through training, while consumers of home-use, kit-type relaxers learn through trial and error.

Like sodium and potassium hydroxides, lithium hydroxide is also an alkali metal hydroxide, and indeed in the 1980s lithium hydroxide was used to formulate commercially successful hair relaxers of the "no-mix" type. Interestingly, those skilled in the relaxer art now make no real distinction among sodium, potassium, and lithium hydroxides as is attested to in the following excerpt from a recent relaxer patent specification (Akhtar et al., U.S. Pat. No. 4,950,485, col 7, in 16): "Alternatively, a cosmetic cream base for use directly as a no-base hair relaxing composition can contain a water-soluble alkaline caustic material which is capable of both bringing the pH of the composition to a value of about 12 to about 14, and acting as the sole hair relaxing agent. Alkali metal hydroxides, including sodium hydroxide, potassium hydroxide and lithium hydroxide may be used as the water-soluble alkaline caustic material. Sodium hydroxide is preferred and may be present in amounts from about 1 to about 3 weight percent of the total composition, preferably from about 1.5 to 2.5 weight percent."

Unlike sodium and potassium hydroxides, however, an aqueous solution of lithium hydroxide is reportedly a "weak electrolyte" (lower electrical conductance), which is evidence of incomplete ionization, which in turn defines lithium hydroxide as a classical "weak base'. Commercial hair relaxers made with lithium hydroxide as the active ingredient typically have pH values of around 12.2 to 12.7; whereas, those made with sodium hydroxide or guanidinium hydroxide generally exceed 13.5. This being the case, one can only guess the answers to the following two questions— (1) If indeed, the hydroxide anion is the species solely responsible for the chemical reactivity of hair relaxer formulations, how can a lithium hydroxide relaxer having a hydroxide ion concentration which is lower by a factor of at least 10 be just as effective in straightening hair as a sodium hydroxide or guanidinium hydroxide relaxer? (2) If the pH is significantly lower, why does the incidence of skin and scalp irritation experienced by users of lithium hydroxide relaxers equal or exceed that of sodium hydroxide relaxer users?

In an attempt to answer the two questions posed above, a search of the technical literature was conducted to locate a value for the dissociation constant for lithium hydroxide:

$$LiOH \longleftrightarrow Li^+ + OH^-$$

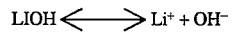

$$K_x = \frac{[Li^+][OH^-]}{[LiOH]} \qquad (Eq. 1)$$

One reference (Darken and Meier) reported K=1.2 based on electrical conducted. Surprisingly, when used to solve Eq. 1, the literature value of K did not predict the pH of lithium hydroxide relaxers (usually about 12.6). Moreover, it did not predict the pH of simple solutions of lithium hydroxide prepared in the laboratory. For example, the aqueous phase of a typical relaxer is about 1 molar in lithium hydroxide. A value for $K_x$ of 1.2 predicts that the pH would be 13.72. When 1 molar lithium hydroxide solutions were prepared in the laboratory, the pH was 13.01. Because the relationship between the pH and the hydroxide concentration of a solution is exponential, a discrepancy in pH of +0.71 of a pH unit represents nearly a 6-fold difference in predicted vs. experimental molar hydroxide concentration.

One explanation for this very large experimental discrepancy is that the value of K=1.2 (based on electrical conductivity) of lithium hydroxide solutions describes something other that the simple dissociation of LiOH into Li$^+$ and OH$^-$ ions.

Although lithium is classified in the periodic chart as an alkali metal, in many respects it is grossly different from sodium and/or potassium. In fact, in all salt-forming reactions, the "ionic" bonds between lithium and oxygen (and other electron-rich atoms) are so strong that these salt bonds behave to a large extent like covalent bonds rather than ionic bonds. For example, lithium stearate (an "alkali metal soap") is only minimally soluble in water; whereas the sodium and potassium stearates are highly soluble. Lithium carbonate is soluble in water only up to about 1.5 gm per 100 gm of water, while sodium and potassium carbonates are extremely water soluble.

If the Li-O bond of LiOH is more like a covalent bond than an ionic one, then a secondary equilibrium can be established whereby hydroxide ions abstract protons from undissociated LiOH molecules to produce a LiO$^-$ species (lithoate) according to the following equation:

$$K_y = \frac{[\text{LiO}^-]}{[\text{LiOH}][\text{OH}^-]} \quad (\text{Eq. 2})$$

Allowing for the formation of LiO$^-$ according to Eq. 2 and combining Eq. 1 with Eq. 2, the following can describe the dissociation of LiOH.

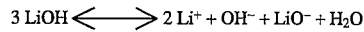

$$K_{xy} = \frac{[\text{Li}^+]^2[\text{OH}^-][\text{LiO}^-]}{[\text{LiOH}]^3} \quad (\text{Eq. 3})$$

An assumption can be made that Eq. 3 (not Eq. 1) now describes a solution of lithium hydroxide in water and that $K_{xy}$ is the dissociation constant determined by Darken and Meier to have a value of 1.2. Based on this assumption, numerical values for $K_x$ and $K_y$ can be calculated to be 0.263 and 17.35, respectively. When these dissociation constants were used to calculate the pH of aqueous solutions that were 1 molar in lithium hydroxide, the equations predicted that the pH was 12.99, which agreed well with the experiment determined value of 13.01. The complete description of all of the soluble species in a 1 molar lithium hydroxide solution is as follows:

OH$^-$=0.143 molar

LiO$^-$=0.357 molar

LiOH=0.144 molar

Li$^+$=0.499 molar pH=12.99

The 1 molar lithium hydroxide solution described above should be compared to an analogous 1 molar sodium hydroxide solution whose soluble species are as follows:

OH$^-$=0.804 molar

NaOH=0.195 molar

Na$^+$=0.804 molar pH=13.74

Clearly, the concentration of hydroxide ion in a 1 molar lithium hydroxide solution is lower by a factor of more than 5 than the hydroxide concentration of an analogous sodium hydroxide solution. Chemists skilled in the art of hair relaxer formulations would certainly agree that if one made a sodium hydroxide relaxer whose aqueous phase contained only 0.143 molar NaOH (0.3 wt. % in the formula), a relaxer so weak would take many hours to relax hair. This being the case, it is likely that the LiO$^-$ (lithoate) species, a base other than hydroxide, is the principal active ingredient in lithium hydroxide relaxers.

In a number of applications-oriented studies, lithium hydroxide has been observed to behave differently than sodium hydroxide and/or potassium hydroxide. For example, lithium hydroxide is sometimes used in the tanning of hides. It is reported to be absorbed into the skins to a greater extent than other alkalis, but it causes less swelling. Because from a chemical viewpoint, hair keratin and skin keratin are very similar, one might expect lithium hydroxide (possibly as lithoate ion) to penetrate the hair shaft more readily and with less swelling than other alkalis. This being the case, one would predict that lithium hydroxide might be a good hair relaxer even though it has a substantially lower hydroxide ion concentration than other types of alkaline relaxers. Moreover, if lithium hydroxide is absorbed readily into animal hides, it might be expected to be absorbed readily into the human skin and scalp; thus, it might be highly irritating to the skin even thought the pH is lower than with other alkalis.

When lithium hydroxide relaxers are made in a manner and by a process analogous to the preparation of sodium hydroxide relaxers, the skin and scalp irritation potential of the resulting emulsions is very high. The incidence of caustic burning is much greater than for sodium hydroxide relaxers having comparable molar concentrations of hydroxide ion. Skilled formulators, however, have discovered that the addition of several percent of calcium oxide or calcium hydroxide to the lithium hydroxide relaxer formulations somehow attenuates the activity of the active chemical species with regard to skin and scalp irritation without compromising hair straightening efficacy. The precise mechanism by which calcium hydroxide and/or calcium ions change the composition is not known, but we can postulate that calcium hydroxide may cause some sort of shift in the chemical equilibrium causing a change in the concentration of one or more of the active species.

With this improvement in the composition of lithium hydroxide relaxers, irritation is lessened to a measurable degree in most batches, but the production process is not highly reproducible and the results in this regard are unpredictable. Many batches still have a very high potential for skin irritation and others have a much lower potential. It has been generally observed that those lithium hydroxide relaxer batches having a high propensity for skin irritation become somewhat milder and less irritating with aging, but the aging time must be on the order of many months or several years. This suggests that lithium hydroxide (with calcium hydroxide) relaxers made by present formulation processes do not quickly and reproducibly reach a thermodynamically stable state. Whatever the reason for the variability and unpredictability of present lithium hydroxide relaxers, these relaxers have achieved far less commercial success than the sodium hydroxide relaxers and the guanidinium hydroxide relaxers.

SUMMARY OF THE INVENTION

The present invention provides compositions and methods for the preparation of certain hair relaxers formulations, which formulations derive their chemical activity from basic and alkaline salts of the alkali metal lithium, and which compositions also require the presence of a partially soluble salt of lithium and a polyvalent anion such as carbonate, sulfate, or phosphate. A process of the present invention comprises contacting a lithium salt (other than lithium hydroxide) with an alkaline earth hydroxide, wherein the anion of the lithium salt is capable of being precipitated by the cation of the alkaline earth hydroxide. Thus, this invention addresses and describes a reactive process for preparing "lithoate" hair relaxers having a very low potential for skin irritation and a very high degree of efficacy with regard to the straightening of curly and/or kinky hair.

The present invention can be considered an improvement over prior art compositions and processes for preparing hair relaxers deriving their chemical reactivity from "lithium hydroxide". The improvement comprises; (1) compositions which contain both "lithium hydroxide" and the lithium salt of a polyvalent anion, and/or (2) the use of a reactive mixture of certain lithium salts and hydroxide salts to prepare the aqueous phase of oil-in-water emulsions such that the compositions and products produced by the process have a low degree of skin irritation from the outset.

It has been found (in a preferred embodiment of this invention) that emulsions prepared using an excess of lithium carbonate and a limited amount of calcium hydroxide as reactive ingredients (instead of the usual lithium hydroxide and calcium oxide) are highly reproducible, highly effective hair relaxer formulations having a very low potential for causing skin irritation during the timeframe (usually no more than 30 minutes) of a traditional relaxer treatment application. Moreover, unlike virtually all prior-art relaxers, the relaxers prepared according to this invention do not totally break down and dissolve hair; therefore, they do not cause or contribute to hair damage and breakage when used.

One skilled in the art will note that the compositions of the present invention may also be used in permanent wave or curling applications. In these latter applications the same advantages are seen as with the straightening process, that is the compositions are effective and cause less irritation than the prior art compositions. Any conventional hair relaxing or hair curling formulation may be used with the substitution of the lithium salt and the alkaline earth hydroxide of the present invention for the active ingredients of the conventional formulation.

DESCRIPTION OF THE PREFERRED EMBODIMENTS

In a preferred embodiment of the process of this invention, an excess of an appropriately selected lithium salt and a predetermined amount of an appropriately selected alkaline earth hydroxide are mixed into the aqueous phase of an appropriately formulated oil-in-water emulsion. A chemical reaction immediately ensues whereby an insoluble salt of the cation of the alkaline earth hydroxide and the anion of the lithium salt precipitates producing an alkaline aqueous phase mostly composed of a solution of soluble ionic and non-ionic lithium compounds.

In a most preferred embodiment of the invention, the lithium salt will be lithium carbonate or lithium sulfate, and the alkaline earth hydroxide will be calcium hydroxide, barium hydroxide, or strontium hydroxide. An appropriate oil-in-water emulsion is an emulsion known to those skilled in the art as acceptable as a cosmetic or hair treating composition. Such compositions may include conventional additives used to provide their ordinary functions. In the most preferred embodiment, the lithium salt is in molar excess of from about 0.01% to about 10%.

The invention can be practiced in at least three different modes. In the description of these modes which follows, the example of lithium carbonate is used to represent all of the lithium salts which work in this process and calcium hydroxide is used to represent all of the alkaline earth hydroxides which work in this process.

In the first mode, the process can be used during batching operations to manufacture one-component, "no-mix" hair relaxers which are highly stable to prolonged storage. In the second mode, calcium hydroxide can be formulated into an emulsion in a manner identical to the preparation of relaxer creams for two-component, "mix-type", guanidinium hydroxide relaxers and lithium carbonate can be packaged and/or formulated as an activator for addition to the relaxer cream by the consumer just prior to the relaxer treatment. In the third mode, an excess of lithium carbonate can be formulated in a relaxer cream that does not contain any calcium hydroxide, and calcium hydroxide can be packaged and/or formulated as an activator for mixing with the relaxer cream by the consumer just prior to the relaxer treatment.

The chemical reactions which underlie the process of this invention are those which are already known to be preferred methods for the synthesis of lithium hydroxide. For example, a simple laboratory mode of preparation is the double decomposition of lithium sulfate and barium hydroxide solutions (Barnes, E., J.C.S., 1931, 2, 605–20).

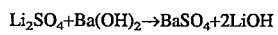

$$Li_2SO_4 + Ba(OH)_2 \rightarrow BaSO_4 + 2LiOH$$

If exactly equivalent quantities of lithium sulfate and barium hydroxide are used, a pure dilute solution of lithium hydroxide remains after filtration.

A widely used process for the commercial production of lithium hydroxide is the causticization of lithium carbonate with lime. The reaction proceeds according to the equation:

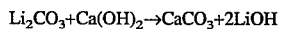

$$Li_2CO_3 + Ca(OH)_2 \rightarrow CaCO_3 + 2LiOH$$

The reactants are slurried together in water and boiled. With a 5% excess of slaked lime present and sufficient water to give a final concentration of 0.3 lb/gal, the conversion is nearly complete. The precipitated chalk is allowed to settle, and the lithium hydroxide solution is decanted. The solution is then evaporated and on cooling yields crystals of lithium hydroxide monohydrate (>99% purity). The major impurity in the product is lithium carbonate formed by the absorption of carbon dioxide from the atmosphere.

Even though the chemical reactions of the preferred embodiment of this invention are those which are known to produce virtually quantitative yields of "lithium hydroxides", it was totally unexpected to discover that, when freshly prepared, hair relaxer formulations containing "lithium hydroxides" prepared in situ were much less irritating than hair relaxer formulations prepared with commercial lithium hydroxide monohydrate, with or without added calcium oxide or calcium hydroxide. In preparing numerous relaxers using lithium carbonate and calcium hydroxide, it was subsequently discovered that those relaxers which were prepared with an excess of the calcium hydroxide became more and more irritating with the passage of several week's time, while those that contained an excess of the lithium carbonate did not become more irritating.

The reasons for this difference are still not completely understood, but laboratory evidence suggests that the difference is manifest in the interaction of soluble yet unreacted polyvalent lithium salts and/or their polyvalent anions with one of the species in the following equilibrium:

$$3LiOH \rightleftharpoons 2Li^+ + OH^- + LiO^- + H_2O$$

Aside from the plethora of Li⁺ ions, which are undoubtedly intimately associated with all anions, the most likely species to interact with polyvalent anions is the undissociated (neutral) LiOH molecules.

Assuming that neutral LiOH interacts with either carbonate or sulfate, one may postulate the formation of complex species such as the following:

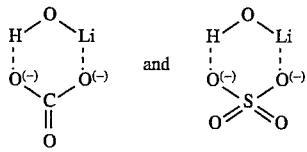

The presence of such complexes in the compositions of the present invention would strongly suggest why these novel hair relaxers have such a low propensity for irritating the skin and scalp. Consider the following:

It is widely accepted that small neutral molecules penetrate the skin more rapidly than solvated ions and intimate ion pairs. Considering that aqueous solutions of lithium hydroxide (and prior art hair relaxers made with "lithium hydroxide") contain a relatively large fraction of undissociated LiOH, one would expect that such solutions could have an abnormally high potential for irritating living skin tissues. On the other hand, if the undissociated LiOH molecules formed stable, large quasi-ionic complexes in the presence of polyvalent anions, one might expect that the irritation potential would be reduced substantially.

The reaction at room temperature of lithium carbonate with calcium hydroxide proceeds rapidly to about 60% of completion and then slows down considerably. Because lithium carbonate is about 10-times more soluble than calcium hydroxide, freshly prepared relaxers of the present invention always contain lithium carbonate, regardless of whether or not an excess of calcium hydroxide is used. The presence of the carbonate moiety could account for the low irritation potential of freshly prepared relaxers. When an excess of calcium hydroxide is used, however, those relaxers eventually become totally depleted of lithium carbonate as the double decomposition reaction goes to completion. Such relaxers then have a higher potential for irritating the skin and scalp. The length of time that it takes for such relaxers to become lithium carbonate depleted depends upon many variable such as the starting concentrations of reactants, the storage temperature, and the consistency (thin or thick) of the relaxer cream.

Unlike those hair relaxers prepared with commercial lithium hydroxide, the order of addition, the formulation/reaction time, and the temperature are not critical parameters affecting the composition or the performance of the relaxers of the present invention. For example, when the prior-art lithium hydroxide relaxers are prepared, care must be taken to ensure that all of the lithium hydroxide monohydrate is completely pre-dissolved in a portion of the water used to make the aqueous phase, that an excess of calcium oxide or calcium hydroxide is added to the lithium hydroxide solution just prior to the addition of this portion to the formulation, and that the lithium hydroxide solution (with slurried lime) is added at about 65° C. after the oil-in-water emulsion has been formed/phased at about 85° C. and the hot formulation is being cooled. In the process of the present invention, lithium carbonate and calcium hydroxide can be added to the aqueous portion of the formulation either at any time prior to heating the mixture to near 85° C. for phasing or after the mixture has been phased and is cooling. Alternatively, either the lithium carbonate or the calcium hydroxide alone can be added to and/or formulated into the emulsion at any stage of the manufacturing process, and the other reactive component can be added as an activator (by the consumer) at any time prior to use.

It should be stressed that it is not imperative that a reactive process utilizing certain polyvalent lithium salts and certain alkaline earth hydroxides be used to form the compositions of the present invention. Rather, certain polyvalent lithium salts, such as lithium carbonate and lithium sulfate, may be mixed directly with commercial lithium hydroxide in the aqueous phase of a suitable oil-in-water emulsion to yield hair relaxers having a low potential for skin irritation. One skilled in the art might also prepare an alkaline aqueous solution (phase) containing lithium hydroxide and then press in some carbon dioxide to produce an effective amount of lithium carbonate in situ.

The relaxer compositions of the present invention not only have a lower potential for causing skin and scalp irritation than prior art "lithium hydroxide" relaxers, they also react differently with hair.

EXAMPLES

While not intended to be limiting in any way the scope of the present invention, the following examples demonstrate embodiments of the present invention.

Example 1 (Formula 2000)

This example illustrates the preparation of a one-component/no-mix hair cream/emulsion. The formula is as follows:

| Ingredients | Weight Percent |
| --- | --- |
| Part A: | |
| Polawax | 8.00 |
| Cetyl Alcohol | 0.50 |
| Stearyl Alcohol | 0.30 |
| PEG-75 Lanolin | 2.00 |
| Petrolatum | 13.55 |
| Mineral Oil | 18.01 |
| Laneth-15 | 0.40 |
| PEG-24 Hydrogenated Lanolin | 0.20 |
| Ethoxylated Soya Sterol | 2.00 |
| Part B: | |
| Water | 41.03 |
| Propylene Glycol | 5.60 |
| Polyol Alkoxy Ester | 1.00 |
| Oleth-3 | 0.30 |
| Lithium Carbonate | 2.80 |
| Calcium Hydroxide | 2.31 |
| Polyquaternium-2 | 2.00 |

Process of making: All of the ingredients of the oil phase (Part A) are mixed in an appropriate stirred vessel and the mixture is heated to 85° C. All of the ingredients of the aqueous phase (Part B), except for the Polquaternium-2, are placed in a vessel outfitted with a homogenizer mixer, and the mixture is heated, with stirring, to 85° C. When both phases have reached their target temperatures, the hot oil phase (Part A) is added to the hot aqueous phase (Part B) and the two-phase is homogenized at high speed for 15 minutes to form a uniformly dispersed oil-in-water emulsion. The emulsion is then cooled to 60° C., at which point it is transferred to a scraper vessel where it is further cooled to 45 ° C. The Polyquaternium-2 is then added, and the finished cream is cooled to room temperature with slow agitation.

The pH of the finished product was 12.3.

The kinky hair of a Negro female was gently combed to remove tangles, and then the hair was parted into four quadrants. A generous amount of the relaxer formulation was applied to the hair on a section-by-section basis. The hair was combed gently after the relaxer was applied to ensure even distribution. When the entire head of hair appeared to be covered with the relaxer cream, the hair was parted with a comb in different sections of the head and checked to ensure that the relaxer formulation had penetrated to the hair root area. Thereafter, all of the hair was smoothed (i. e., straightened) frequently using hands or the back of a plastic comb until the desired degree of straightness was achieved.

The hair was rinsed thoroughly with warm water until all of the relaxer cream was removed. Then the hair was shampooed with a buffered, pH 5 neutralizing shampoo, treated with a rinse-out protein conditioner, towelled dry, and set.

The hair treated with the formulation in this example had a permanent straightening effect, which lasted until new growth appeared at the hair roots. Although this relaxer formulation touched the individual's scalp in numerous places for the duration of the treatment (about 20 minutes), there were no complaints of skin irritation and burning (a problem which "always" occurs when this individual uses most commercially available products).

Example 2

This example demonstrates the preparation of a one-component/no-mix hair relaxer/emulsion with about 10% faster reactivity with hair than the composition of Example 1. The formula is as follows:

| Ingredients | Weight Percent |
| --- | --- |
| Part A: | |
| Polawax | 8.00 |
| Cetyl Alcohol | 0.50 |
| Stearyl Alcohol | 0.30 |
| PEG-75 Lanolin | 2.00 |
| Petrolatum | 13.38 |
| Mineral Oil | 17.32 |
| Laneth-15 | 0.40 |
| PEG-24 Hydrogenated Lanolin | 0.20 |
| Ethoxylated Soya Sterol | 2.00 |
| Part B: | |
| Water | 41.40 |
| Propylene Glycol | 5.60 |
| Polyol Alkoxy Ester | 1.00 |
| Oleth-3 | 0.30 |
| Lithium Carbonate | 2.80 |
| Calcium Hydroxide | 2.80 |
| Polyquaternium-2 | 2.00 |

The process of making was exactly the same as in Example 1, and the pH of the finished product was 12.4.

Then this relaxer cream was applied to the hair of Negro women, the results were the same as for Example 1 except the processing time was about 10% shorter for the same hair types (i.e., fine, medium, and coarse).

Example 3

This example illustrates the preparation of a one-component/no-mix hair relaxer cream/emulsion with about 10% faster reactivity with hair than Example 2. The formula is as follows:

| Ingredients | Weight Percent |
| --- | --- |
| Part A: | |
| Polawax | 8.00 |
| Cetyl Alcohol | 0.50 |
| Stearyl Alcohol | 0.30 |
| PEG-75 Lanolin | 2.00 |
| Petrolatum | 13.30 |
| Mineral Oil | 17.07 |
| Laneth-15 | 0.40 |
| PEG-24 Hydrogenated Lanolin | 0.20 |
| Ethoxylated Soya Sterol | 2.00 |
| Part B: | |
| Water | 43.00 |
| Propylene Glycol | 5.60 |
| Polyol Alkoxy Ester | 1.00 |
| Oleth-3 | 0.30 |
| Lithium Carbonate | 3.30 |
| Calcium Hydroxide | 2.83 |
| Hydroxypropyl Bis-stearyldimonium Chloride | 0.20 |

The process of making was the same as for Example 1, and the pH of the finished product was 12.3.

When this relaxer cream was applied to the hair of Negro women, the results were the same as for Example 2 except the processing time was about 10% shorter for the same hair types (i.e., fine, medium, and coarse). Moreover, approximately one-tenth of all individuals on whom this relaxer formulation was applied complained of mild to moderate skin and scalp irritation.

Example 4

This example represents the preparation of a two-component hair relaxer formulation containing Calcium Hydroxide in the relaxer base component (Component I) and Lithium Carbonate in the activator component (Component II).

| Ingredients | Weight Percent |
| --- | --- |
| Part A: | |
| Polawax | 8.00 |
| Catyl Alcohol | 0.50 |
| Stearyl Alcohol | 0.30 |
| PEG-75 Lanolin | 2.00 |
| Petrolatum | 15.78 |
| Mineral Oil | 19.32 |
| Laneth-15 | 0.40 |
| PEG-24 Hydrogenated Lanolin | 0.20 |
| Ethoxylated Soya Sterol | 2.00 |
| Part B: | |
| Water | 45.40 |
| Polyol Alkoxy Ester | 1.00 |
| Oleth-3 | 0.30 |
| Calcium Hydroxide | 2.80 |
| Polyquaternium-2 | 2.00 |
| Component II: | |
| Propylene Glycol | 56.00 |
| Lithium Carbonate | 40.00 |
| Fumed Silica | 3.00 |
| Titanium Dioxide | 1.00 |

Process of making: Add Propylene Glycol to the kettle and begin moderate agitation with a high-speed Cowls disperser blade. Add Lithium Carbonate slowly until addition is complete. Continue disperser action and add Fumed Silica and Titanium Dioxide. Continue mixing for 30 minutes.

An activated relaxer cream is prepared by mixing about 250 grams of Component I with 20 grams of Component II. Accurate measuring is required. The relaxer is ready to use in about 15 minutes after mixing. Moreover, the relaxer can be safely used without fear of irritation for at least one year after it is made. This is compared to the two-component relaxers deriving their activity from guanidine hydroxide of the prior art, which must be used within about four hours after they mixed.

Example 5

This example represents the preparation of a two-component hair relaxer formulation containing Lithium Carbonate in the relaxer base component (Component I) and Calcium Hydroxide in the activator component (Component II).

Component I

| Ingredients | Weight Percent |
| --- | --- |
| Part A: | |
| Cosmowax J | 10.50 |
| Petrolatum | 10.75 |
| Mineral Oil | 10.75 |
| Ethoxylated Soya Sterol | 1.00 |
| Part B: | |
| Water | 59.69 |
| Lithium Carbonate | 3.30 |
| PPG-12-PEG-65 Lanolin Oil | 3.00 |
| Succinic Acid | 0.25 |
| Part C: | |
| PPG-B-Ceteth-10 Phosphate | 1.50 |
| Part D: | |
| Tropaeolin O | 0.0015 |
| Water | 0.0585 |

Process of making: Add Part A ingredients to the homomixer kettle and begin heating with moderate agitation to 80° C. Add Part B ingredients to the scraper kettle and begin heating with moderate agitation to 80° C. When Part A and Part B reach 80° C., slowly add Part B to Part A and homomix with moderate agitation for 15 minutes. Transfer batch back to scraper kettle and begin cooling with chilled water and moderate scraper agitation. When batch cools to 45° C., add Part C. Prepare Part D and add it to the batch when the temperature reaches 40° C. Continue cooling to 33° C. Component I is pastel yellow in color and the pH is about 10.

Component II

| Ingredients | Weight Percent |
| --- | --- |
| Propylene Glycol | 51.00 |
| Calcium Hydroxide | 45.00 |
| Fumed Silica | 3.00 |
| Titanium Dioxide | 1.00 |

Process: Add Propylene Glycol to the kettle and begin moderate agitation with a high-speed Cowls disperser blade. Add Calcium Hydroxide slowly until addition is complete. Continue disperser action and add Fumed Silica and Titanium Dioxide. Continue for 30 minutes.

An activated relaxer cream is prepared by mixing about 200 to 300 parts of Component I with 20 to 30 parts of Component II. Accurate measuring is not required; the final concentration of active ingredients will be determined by the concentration of Lithium Carbonate in Component I. Continue mixing until the color changes from yellow to pink/peach indicating that the pH of the mixture has increased to above pH 12. The relaxer is ready to use in about 15 minutes after mixing. Moreover, the relaxer can be safely used without fear of irritation for at least one week after mixing. Again, this is compared to the two-component relaxers deriving their activity from guanidine hydroxide, which must be used within about four hours after they are mixed.

Example 6

This example represents the preparation of a one-component, no-mix lithium relaxer cream having a stoichiometric excess of Calcium Hydroxide relative to Lithium Carbonate.

| Ingredients | Weight Percent |
| --- | --- |
| Part A: | |
| Polawax | 8.00 |
| Cetyl Alcohol | 0.50 |
| Stearyl Alcohol | 0.30 |
| PEG-75 Lanolin | 2.00 |
| Petrolatum | 13.75 |
| Mineral Oil | 15.85 |
| Laneth-15 | 0.40 |
| PEG-24 Hydrogenated Lanolin | 0.20 |
| Ethoxylated Soya Sterol | 1.00 |
| Part B: | |
| Water | 43.00 |
| Propylene Glycol | 5.60 |
| Polyol Alkoxy Ester | 1.00 |
| Oleth-3 | 0.30 |
| Lithium Carbonate | 2.80 |
| Calcium Hydroxide | 5.10 |
| Hydroxypropyl Bis-stearyldimonium Chloride | 0.20 |

The process was essentially the same as for Example 1; the pH of the cream was 12.9.

When this formulation was used 48 hours after preparation to relax kinky Negro hair, the results initially were identical to Example 2. However, around two weeks after preparation, this formulation developed a very high degree of irritancy. Two individuals had severe scalp irritation after only 5 minutes of application. In forearm skin patch tests for irritation, six of seven participants had to remove the aged product of this example in less than 15 minutes due to severe burning. In contrast, these same seven participants allowed the products of Examples 1 and 2 to remain on their forearms for 30 minutes with no redness or irritation.

Thus, it is clear that the lithium salt must be in excess to the alkaline earth hydroxide to produce a lithium relaxer which has a stable low-irritancy factor over moderate to long term storage.

Example 7

This example represents the preparation of a one-component "prior art" relaxer deriving its activity from Lithium Hydroxide.

| Ingredients | Weight Percent |
| --- | --- |
| Part A: | |
| Polawax | 8.00 |
| Cetyl Alcohol | 0.50 |
| Stearyl Alcohol | 0.20 |
| Petrolatum | 22.00 |
| Mineral Oil | 15.30 |
| Part B: | |
| PEG-75 Lanolin | 0.40 |
| Laneth-15 | 0.20 |
| PEG-24 Hydrogenated Lanolin | 1.00 |
| Part C: | |
| Water | 27.30 |
| Propylene Glycol | 5.60 |
| Hydroxypropyl Bis-stearyldimonium Chloride | 0.10 |
| Part D: | |
| Lithium Hydroxide Monohydrate | 2.90 |
| Deionized Water | 14.20 |
| Part E: | |
| Calcium Oxide | 1.80 |
| Part F: | |
| Fragrance | 0.20 |
| Potassium Coco Hydrolyzed Animal Protein | 0.30 |

Process of making:

1. Weigh out the water and Lithium Hydroxide for Part D and begin mixing in a separate stainless steel pot with a propeller mixer.
2. Weigh out the Part B ingredients in another stainless steel kettle and begin heating to 85° C.
3. Weigh out Part A ingredients in a separate homomixer kettle and begin heating to 85° C. with moderate agitation.
4. Weigh out Part C ingredients in a separate stainless steel kettle and begin heating to 85° C.
5. When both Part A and Part B reach 85° C., add Part B to Part A and let mix for 10 minutes.
6. With Part A/B and Part C at 85° C., slowly pump Part C into Parts A/B and let mix for 10 minutes with moderate agitation. After 10 minutes, begin cooling the batch with tap water in the jacket of the kettle.
7. Add Part E to Part D and pre-mix well. (Note: Part D must be fully dissolved before adding to the batch. Part E is to be added to Part D just before adding to the batch.)
8. When the batch temperature reaches 65° C., shut off the tap water cooling to the kettle and drain the jacket. Add the Lithium Hydroxide/Calcium Oxide slurry (Parts D/E) to the batch and continue mixing for 10 minutes with moderate homomixer agitation. (Note: Continue to stir Part D/E with a large metal spatula while adding it to the batch).
9. Pump the mixture into the scraper kettle and begin cooling to 40° C. with moderate scraper agitation. (Note: The scraper kettle should be chilled with cold water before the batch transfer).
10. Premix the Part F ingredients and add Part F to the batch when the temperature is 40° C. Continue mixing until the batch is smooth and creamy or until the batch reaches 35° C.

The pH of the formulations made by this example typically range from 11 to 12.

When these prior art relaxers are used to straighten kinky Negro hair by the process described in Example 1, good straightening results are generally obtained. Skin and scalp irritation occurs regularly, with about the same frequency as aged formulations prepared according to Example 4.

Example 8

This example addresses whether or not the reactive process of this invention is broadly applicable to reducing the irritation level of all alkali-metal hydroxide relaxers or just those deriving their activity from lithium. Apparently, the reactive process using alkali carbonates and calcium hydroxide does indeed reduce the irritancy of the resulting relaxers.

Six relaxers were prepared according to Example 6 except that in five cases either lithium hydroxide monohydrate, potassium hydroxide, potassium carbonate, sodium hydroxide, or sodium carbonate, respectively, were substituted in molar equivalent amounts for lithium carbonate. The Table below shows the specific weight percent substitutions and the values of pH of the relaxers.

| Chemical | Formula Wt. | Mole % | Wt. % | pH |
| --- | --- | --- | --- | --- |
| Lithium Carbonate | 73.89 | 0.038 | 2.80 | 12.9 |
| Lithium Hydroxide | 41.94 | 0.076 | 3.179 | 12.15 |
| Potassium Carbonate | 138.21 | 0.038 | 5.252 | 13.22 |
| Potassium Hydroxide | 65.23 | 0.076 | 4.958 | 13.47 |
| Sodium Carbonate | 124.00 | 0.038 | 4.712 | 13.00 |
| Sodium Hydroxide | 40.00 | 0.076 | 3.04 | 13.69 |

Approximately 48 hours after each of the above relaxers were prepared, a test panel of 8 individuals tested their irritancy using a forearm patch test. The test formulations were applied to different sites on the forearm and left there for 25 minutes (or less if burning occurred). The following Table summarizes the results.

| Chemical | Stinging/Burning | Redness |
| --- | --- | --- |
| Lithium Carbonate | 1 of 8 mild itch/sting | 3 of 8 slight red |
| Lithium Hydroxide | 1 of 8 mild itch/sting | 7 of 8 slight red |
| Potassium Carbonate | 3 of 8 moderate sting | 5 of 8 slight red |
| Potassium Hydroxide | 6 of 8 moderate sting 2 of 8 severe burn | 6 of 8 very red 2 of 8 tissue burn |
| Sodium Carbonate | 2 of 8 mild itch/sting | 3 of 8 slight red |
| Sodium Hydroxide | 3 of 8 mild itch/sting | 6 of 8 very red |

Example 9

We provide here examples of how alternative lithium salts and alkaline earth metal hydroxides can be used in the present invention.

| Formula: Ingredients | 9A | 9B | 9C | 9D |
| --- | --- | --- | --- | --- |
| | Weight Percent | | | |
| Part A: | | | | |
| Polawax | 8.00 | 7.00 | 8.00 | 8.00 |
| Cetyl Alcohol | 0.50 | 0.50 | 0.50 | 0.50 |
| Stearyl Alcohol | 0.30 | 0.30 | 0.30 | 0.30 |
| PEG-75 Lanolin | 2.00 | 2.00 | 2.00 | 2.00 |
| Petrolatum | 13.34 | 12.34 | 13.35 | 14.05 |
| Mineral Oil | 16.15 | 14.26 | 15.66 | 16.85 |
| Laneth-15 | 0.40 | 0.40 | 0.40 | 0.40 |
| PEG-24 Hydrogenated | 0.20 | 0.20 | 0.20 | 0.20 |

-continued

| Formula: Ingredients | 9A | 9B | 9C | 9D |
|---|---|---|---|---|
| | Weight Percent | | | |
| Lanolin Ethoxylated Soya Sterol | 1.00 | 1.00 | 1.00 | 1.00 |
| Part B: | | | | |
| Water | 45.40 | 41.36 | 32.89 | 45.40 |
| Propylene Glycol | 2.80 | 2.80 | 2.80 | 2.80 |
| Hydroxypropyl Bis-stearyldimonium Chloride | 0.20 | 0.20 | 0.20 | 0.20 |
| Lithium Carbonate | — | — | — | 2.80 |
| Lithium Sulfate | 4.21 | 4.21 | 4.21 | — |
| Calcium Hydroxide | 5.10 | — | — | 5.10 |
| Barium Hydroxide Monohydrate | — | 13.03 | — | — |
| Strontium Hydroxide Octahydrate | — | — | 18.29 | — |
| Part C: | | | | |
| Fragrance | 0.10 | 0.10 | 0.10 | 0.10 |
| Potassium Coco-Hydrolyzed Animal Protein | 0.30 | 0.30 | 0.30 | 0.30 |

These formulas were evaluated using a laboratory method to test their efficacy as hair straighteners, i.e. the Percent Relaxation imparted to Negro hair fibers and the Percent Reversion of these relaxed fibers at high humidity. The results summarized in the Table below show that three of the four formulations are highly efficacious. Hair fibers treated with Formula 9A (the one prepared with Lithium Sulfate and Calcium Hydroxide) had a unacceptable degree of reversion. This is most likely due a poor yield of active ingredients deriving from the high degree of solubility of Calcium Sulfate.

| Formula | OH Source | Li Salt | Relaxation, % | Reversion % |
|---|---|---|---|---|
| 9A | Calcium | Sulfate | 97.6 ± 0.7 | 16.3 ± 7.4 |
| 9B | Barium | Sulfate | 97.8 ± 0.0 | 0.4 ± 0.6 |
| 9C | Strontium | Sulfate | 98.0 ± 0.1 | 2.6 ± 3.0 |
| 9D | Calcium | Carbonate | 98.2 ± 0.6 | 1.8 ± 2.3 |

Example 10

Three "prior art" Lithium Hydroxide relaxer formulations were prepared to determine whether or not the inclusion of Lithium Carbonate in the formulation (as taught in French Patent 1,553,084) would render the formulations less irritating. The specific formulas were as follows:

| Formula: Ingredients | 10A | 10B | 10C |
|---|---|---|---|
| | Weight Percent | | |
| Part A: | | | |
| Polawax | 8.00 | 8.00 | 8.00 |
| Cetyl Alcohol | 1.20 | 1.20 | 1.20 |
| Stearyl Alcohol | 0.80 | 0.80 | 0.80 |
| Petrolatum | 21.90 | 22.20 | 21.20 |
| Mineral Oil | 16.40 | 15.10 | 15.10 |
| Part B: | | | |
| PEG-75 Lanolin | 0.40 | 0.40 | 0.40 |
| Laneth-15 | 0.20 | 0.20 | 0.20 |
| PEG-24 Hydrogenated Lanolin | 1.00 | 1.00 | 1.00 |
| Part C: | | | |

-continued

| Formula: Ingredients | 10A | 10B | 10C |
|---|---|---|---|
| | Weight Percent | | |
| Deionized Water | 27.30 | 27.30 | 27.30 |
| Propylene Glycol | 5.60 | 5.60 | 5.60 |
| Hydroxypopyl Bis-stearyldimonium Chloride | 0.10 | 0.10 | 0.10 |
| Part D: | | | |
| Lithium Hydroxide Monohydrate | 2.90 | 2.90 | 2.90 |
| Deionized Water | 14.20 | 14.20 | 14.20 |
| Part E: | | | |
| Lithium Carbonate | — | 1.00 | 2.00 |
| pH | 12.7 | 12.6 | 12.6 |

All of the formulas were prepared by the process of Example 7. In forearm patch tests for irritancy, all three of the above formulas caused the same degree of stinging and redness. Thus, the prior art lithium hydroxide relaxers, even with the addition of lithium carbonate, do not produce the successful formulations of the present invention.

Example 11

This example addresses relaxers formulated essentially as Example 10 except that polyprotic acids (sulfuric and phosphoric) were used to generate Lithium Sulfate and Lithium Phosphate in situ. Note that the Lithium Hydroxide concentration was increased to provide a molar equivalent amount of LiOH to react with the acids.

| Formula: Ingredients: | 11A | 11B | 11C |
|---|---|---|---|
| | Weight Percent | | |
| Part A: | | | |
| Polawax | 8.00 | 8.00 | 8.00 |
| Cetyl Alcohol | 1.20 | 1.20 | 1.20 |
| Stearyl Alcohol | 0.80 | 0.80 | 0.80 |
| Petrolatum | 22.00 | 22.00 | 22.00 |
| Mineral Oil | 14.10 | 14.10 | 14.10 |
| Part B: | | | |
| PEG-75 Lanolin | 0.40 | 0.40 | 0.40 |
| Laneth-15 | 0.20 | 0.20 | 0.20 |
| PEG-24 Hydrogenated Lanolin | 1.00 | 1.00 | 1.00 |
| Part C: | | | |
| Deionized Water | 16.99 | 18.48 | 16.24 |
| Propylene Glycol | 5.60 | 5.60 | 5.60 |
| Hydroxypropyl Bis-stearyldimonium Chloride | 0.10 | 0.10 | 0.10 |
| Part D: | | | |
| Lithium Hydroxide Monohydrate | 2.90 | 2.90 | 2.90 |
| Deionized Water | 14.20 | 14.20 | 14.20 |
| Part E: | | | |
| Lithium Hydroxide Monohydrate | 1.14 | 5.17 | 1.70 |
| Sulfuric Acid (96.7%) | 1.37 | 2.75 | — |
| Phosphoric Acid | — | — | 1.56 |
| pH | 12.3 | 12.4 | 12.4 |

All of the formulas were prepared by the process of Example 7. In forearm patch tests for irritancy, all three of the above formulas caused the same degree of stinging and redness.

We claim:

1. A method for the production of a one-component, stable and non-irritating lithium relaxer formulation comprising:
   a) providing an oil-in-water emulsion;
   b) adding a lithium salt and an alkaline earth metal hydroxide to the emulsion, wherein the lithium salt is in molar excess to the alkaline earth metal hydroxide and wherein the lithium salt is selected from the group consisting of lithium carbonate, lithium sulfate, and lithium phosphate, and the alkaline earth metal hydroxide is selected from the group consisting of calcium hydroxide, barium hydroxide, and strontium hydroxide.

2. A method for the production of a two-component, stable and non-irritating lithium relaxer formulation comprising:
   a) providing an oil-in-water emulsion;
   b) adding an alkaline earth metal hydroxide to the emulsion;
   c) providing a lithium salt as an activator for mixing with the emulsion to form the relaxer formulation; wherein the lithium salt is in molar excess to the alkaline earth hydroxide in the relaxer formulation and wherein the lithium salt is selected from the group consisting of lithium carbonate, lithium sulfate, and lithium phosphate, and the alkaline earth metal hydroxide is selected from the group consisting of calcium hydroxide, barium hydroxide, and strontium hydroxide.

3. A method for the production of a two-component, stable and non-irritating lithium relaxer formulation comprising:
   a) providing an oil-in-water emulsion;
   b) adding a lithium salt to the emulsion;
   c) providing an alkaline earth hydroxide as an activator for mixing with the emulsion to form the relaxer formulation; wherein the lithium salt is in molar excess to the alkaline earth metal hydroxide in the relaxer formulation and wherein the lithium salt is selected from the group consisting of lithium carbonate, lithium sulfate, and lithium phosphate, and the alkaline earth metal hydroxide is selected from the group consisting of calcium hydroxide, barium hydroxide, and strontium hydroxide.

4. A method of straightening hair, said method comprising:
   a) contacting the hair with an aqueous composition comprising the reaction products formed by reacting, in an aqueous medium, a lithium salt and an alkaline earth metal hydroxide, wherein the lithium salt is in molar excess to the alkaline earth metal hydroxide and wherein the lithium salt is selected from the group consisting of lithium carbonate, lithium sulfate, and lithium phosphate, and the alkaline earth metal hydroxide is selected from the group consisting of calcium hydroxide, barium hydroxide, and strontium hydroxide,
   b) maintaining the hair under tension, and
   c) removing said composition from the hair.

5. The method of claim 4 wherein the lithium salt is lithium carbonate.

6. The method of claim 4 wherein the alkaline earth metal hydroxide is calcium hydroxide.

7. A method of straightening hair, said method comprising:
   a) providing an oil-in-water emulsion;
   b) adding a lithium salt and an alkaline earth metal hydroxide to the emulsion to form a hair straightening composition, wherein the alkaline earth metal hydroxide is in molar excess to the alkaline earth hydroxide and wherein the lithium salt is selected from the group consisting of lithium carbonate, lithium sulfate, and lithium phosphate, and the alkaline earth metal hydroxide is selected from the group consisting of calcium hydroxide, barium hydroxide, and strontium hydroxide;
   c) applying said composition to the hair which is maintained under tension for the period of time necessary to accomplish the straightening of the hair; and
   d) removing the composition from the hair.

8. A kit for use in straightening hair comprising a first ingredient and a second ingredient, which are disposed in separate containers and which are combined to produce the hair straightening composition;
   a) wherein the first ingredient is an oil-in-water emulsion which comprises an alkaline earth metal hydroxide, and
   b) wherein the second ingredient is an activator which comprises a lithium salt, wherein the lithium salt is in molar excess to the alkaline earth metal hydroxide in the hair straightening composition and wherein the lithium salt is selected from the group consisting of lithium carbonate, lithium sulfate, and lithium phosphate, and the alkaline earth metal hydroxide is selected from the group consisting of calcium hydroxide, barium hydroxide, and strontium hydroxide.

9. A kit for use in straightening hair comprising a first ingredient and a second ingredient, which are disposed in separate containers which are combined to produce the hair straightening composition;
   a) wherein the first ingredient is an oil-in-water emulsion which comprises a lithium salt, and
   b) wherein the second ingredient is an activator which comprises an alkaline earth metal hydroxide, wherein the lithium salt is in molar excess to the alkaline earth metal hydroxide in the hair straightening composition and wherein the lithium salt is selected from the group consisting of lithium carbonate, lithium sulfate, and lithium phosphate, and the alkaline earth metal hydroxide is selected from the group consisting of calcium hydroxide, barium hydroxide, and strontium hydroxide.

* * * * *